United States Patent
Perera et al.

(12) 
(10) Patent No.: US 6,544,783 B1
(45) Date of Patent: Apr. 8, 2003

(54) POLYNUCLEOTIDE SEQUENCES FROM RICE

(76) Inventors: J. Ranjan Perera, 6574 Scaup St., Carlsbad, CA (US) 92009; Min Lu, 8866 Stargaze Ave., San Diego, CA (US) 92129; Animesh Ray, 13354 Benchley Rd., San Diego, CA (US) 92130

(*) Notice: Subject to any disclaimer, the term of this patent is extended or adjusted under 35 U.S.C. 154(b) by 0 days.

(21) Appl. No.: 09/843,472

(22) Filed: Apr. 26, 2001

Related U.S. Application Data

(60) Provisional application No. 60/253,925, filed on Nov. 29, 2000, provisional application No. 60/237,736, filed on Oct. 3, 2000, provisional application No. 60/227,231, filed on Aug. 23, 2000, provisional application No. 60/218,366, filed on Jul. 13, 2000, provisional application No. 60/217,891, filed on Jul. 12, 2000, and provisional application No. 60/199,870, filed on Apr. 26, 2000.

(51) Int. Cl.⁷ ............... C12N 15/63; C07H 21/04
(52) U.S. Cl. ............... 435/320.1; 536/23.1; 536/24.1
(58) Field of Search ............... 435/320.1; 536/23.1, 536/24.1

(56) References Cited

PUBLICATIONS

Nakamura et al. Four rice genes encoding cysteine synthase: isolation and differential responses to sulfur, nitrogen and light., Gene, vol. 229(1–2): 155–161, 1999.*

* cited by examiner

*Primary Examiner*—Terry McKelvey
*Assistant Examiner*—William Sandals
(74) *Attorney, Agent, or Firm*—Saliwanchik, Lloyd & Saliwanchik

(57) ABSTRACT

The present invention provides polynucleotides isolated from eucaryotic organisms which are structural genes or promoters. Such isolated polynucleotides are particularly useful in the modification of gene expression in plants. This invention also relates to compositions isolated from plants and their use in the modification of gene activation and/or expression. In a specific embodiment, the subject invention provides plant polynucleotide sequences enconding promoters that are components of the cellular activation and transcription apparatus and the use of such polynucleotide sequences in the modification of expression of genes.

7 Claims, No Drawings

POLYNUCLEOTIDE SEQUENCES FROM RICE

CROSS-REFERENCE TO RELATED APPLICATIONS

This application claims priority to U.S. Provisional Application 60/199,870, filed Apr. 26, 2000; U.S. Provisional Application 60/217,891, filed Jul. 12, 2000; U.S. Provisional Application 60/218,366, filed Jul. 13, 2000; U.S. Provisional Application 60/227,231, filed Aug. 23, 2000; U.S. Provisional Application 60/237,736; filed Oct. 3,2000; and U.S. Provisional Application 60/253,925, filed Nov. 29, 2000. The disclosures, tables, figures, and sequences disclosed within each of these applications is hereby incorporated by reference in their entireties.

BACKGROUND OF THE INVENTION

The domestication of rice has been a very important factor in development of civilization in many parts of the world. Rice is intimately involved in the culture, as well as the food and economy, of many societies. For example, according to folklore, when the Kachins of northern Myanmar (Burma) were sent forth from the center of the Earth, they were given the seeds of rice. Rice is an integral part of their creation myth and remains today as their leading crop and most preferred food. In Bali, it is believed that the Lord Vishnu caused the Earth to give birth to rice, and the God Indra taught the people how to raise it. In both tales, rice is considered a gift of the gods, and even today in both places, rice is treated with reverence.

Chinese myth, by contrast, tells of rice seeds being brought to hungry flood survivors on the tail of a dog. The people planted these seeds, rice grew, and hunger disappeared. Throughout China today, tradition holds that "the precious things are not pearls and jade but the five grains", of which rice is first.

According to Shinto belief, the Emperor of Japan is the living embodiment of Ninigo-no-mikoto, the god of the ripened rice plant. While most modern Japanese may intellectually dismiss this supernatural role, they cannot deny the enormous cultural importance of rice on life in their country - and so it is in much of the rice world (Huke, R. E. and E. H. Huke [1990] "Rice: Then and Now", International Rice Research Institute).

A greater understanding of rice and an enhanced ability to develop improved phenotypes would be of great value to mankind. Also, of great value to mankind would be improved methods of controlling and directing gene expression generally in eukaryotes, and particularly in plants.

Cultivated rices belong to two species, *O. sativa* and *O. glaberrima*. Of the two, *O. sativa* is by far the more widely utilized. *O. sativa* is a complex group composed of two forms endemic to Africa but not cultivated, and a third from, *O. rufipogon*, having distinctive partitions into South Asian, Chinese, New Guinean, Australian, and American forms.

Gene expression in rice, as well as other cells, is a biological function that may be regulated by the cellular processes involved in transcription. During transcription, a single-stranded RNA complementary to the DNA sequence to be transcribed is formed by the action of RNA polymerases. Initiation of transcription in eukaryotic cells is regulated by complex interactions between cis-acting DNA motifs, located within the gene to be transcribed, and trans-acting protein factors. Among the cis-acting regulatory regions are sequences of polynucleotides, termed promoters, enhancers or repressors that are located upstream, or downstream in the case of some elements, to the transcription initiation site. Promoters usually consist of proximal elements (e.g., TATA box) and more distant elements (e.g. CCAAT box). Enhancers are cis-acting DNA motifs that are located further up- and/or down-stream from the initiation site.

Both promoters and enhancers are generally composed of several discrete, often redundant elements, each of which may be recognized by one or more trans-acting regulatory proteins, known as transcription factors. Regulation of the complex patterns of gene expression observed both spatially and temporally, in all developing organisms, is thought to arise from the interaction of enhancer- and promoter-bound, general and tissue-specific transcription factors with DNA (Izawa et al., 1993; Menkens et al., 1995).

The ability to specifically inhibit gene function in a variety of organisms utilizing antisense RNA or ds RNA-mediated interference is well known in the fields of molecular biology (see for example C. P. Hunter, Current Biology [1999] 9:R440–442; Hamilton et al., [1999] Science, 286:950–952; and S. W. Ding, Current Opinions in Biotechnology [2000] 11:152–156, hereby incorporated by reference in their entireties). dsRNA (RNAi) typically comprises a polynucleotide sequence identical or homologous to a target gene (or fragment thereof) linked directly, or indirectly, to a polynucleotide sequence complementary to the sequence of the target gene (or fragment thereof). The dsRNA may comprise a polynucleotide linker sequence of sufficient length to allow for the two polynucleotide sequences to fold over and hybridize to each other; however, a linker sequence is not necessary. The linker sequence is designed to separate the antisense and sense strands of RNAi significantly enough to limit the effects of steric hindrances and allow for the formation of dsRNA molecules and should not hybridize with sequences within the hybridizing portions of the dsRNA molecule.

The specificity of this gene silencing mechanism appears to be extremely high, blocking expression only of targeted genes, while leaving other genes unaffected. A recent example of the use of RNAi to inhibit genetic function in plants used *Agrobacterium tumefaciens*-mediated transformation of *Arabidopsis thaliana* (Chuang, C.-F. and E. M. Meyerowitz [2000], Proc. Natl. Acad. Sci. USA 97:4985–4990). Chuang et aL describe the construction of vectors delivering variable levels of RNAi targeted to each of four genes involved in floral development. Severity of abnormal flower development varied between transgenic lines. For one of the genes, AGAMOUS (AG), a strong correlation existed between declining accumulation of mRNA and increasingly severe phenotypes, suggesting that AG-specific endogenous mRNA is the target of RNAi.

For the development of transgenic plants with desirable traits, constitutive promoters, tissue and organ specific promoters, and cell type specific promoters are required to drive most of the transgenes. The most widely used constitutive plant promoter is derived from the cauliflower mosaic virus. Therefore, there is an urgent need to discover other tissue specific, organ specific, cell specific and constitutive promoters for transgenic applications.

BRIEF SUMMARY OF THE INVENTION

The present invention provides polynucleotides which encode useful proteins and/or are involved in regulation of gene expression. In a preferred embodiment, the isolated polynucleotides of the subject invention are useful in the modification of gene expression in plants. In a specific embodiment, these sequences can be used to modify gene expression in rice. Specifically exemplified herein are sequences which are particularly applicable to gene expression in rice roots.

In one embodiment, the subject invention provides 5' cis regulatory DNA sequences isolated from rice (*Oriza sativa*). These sequences can be used in the modification of gene activation and/or expression in eukaryotes, particularly in rice and in other monocots. Promoters provided herein can be used in the modification of expression of genes by virtue of their role as components of the cellular activation and transcription apparatus. Many of these promoters are "tissue specific". As would be understood by one skilled in the art, these promoters can be used to preferentially express gene product in a particular tissue.

The isolated polynucleotides of the subject invention are useful in the modification of gene expression in plants, since both tissue- and temporal- specific gene expression patterns have been shown to be initiated and controlled by promoters during the natural development of a plant. Thus, targeting of these genes can be exploited in the process of developing desirable plant phenotypes.

Purifed nucleotide sequences of this invention have numerous applications in techniques known to those skilled in the art of molecular biology having the benefit of the instant disclosure. These techniques include their use as hybridization probes, for chromosome and gene mapping, in PCR technologies, and in the production of sense or antisense nucleic acids.

The subject invention also provides novel methods and compositions for controlling gene expression in plants which utilize the polynucleotide sequences disclosed within the sequence listing. Particularly, the polynucleotides disclosed herein are useful as target genes for the synthesis of antisense RNA or dsRNA useful for RNA-mediated gene interference.

The dsRNA arising from the practice of this aspect of the invention are useful for the study of gene function in vivo, specific down-regulation of a target gene, investigation of gene function, and the discovery and manipulation of biological processes and pathways. By way of example, biosynthetic pathways may be manipulated by the practice of this invention by inactivation of specific gene products, such as enzymes, to allow for the accumulation of intermediate biosynthetic products.

Another use of the ssRNA and/or dsRNA provided by this aspect of the invention concerns the identification of genomic loci useful for the insertion of transgenes in the genome of a plant. In this embodiment of the invention, plants are evaluated using ssRNA and/or dsRNA provided for by this aspect of the invention and examined for phenotypic change. It is well recognized in the art that the incorporation of transgenes into the genome of a transformed plant or animal can result in the inactivation of a gene. When such an event occurs, the transformed plant or animal can suffer deleterious side effects (such as reduced viability, decreased vigorousness of growth, or increased/uncontrolled cell growth), evidence phenotypic changes, or die. Thus, where the ssRNA and/or dsRNA administered to the plant or animal does not cause death, deleterious effects, or phenotypic changes upon the treated plant or animal, a site for the insertion of a transgene has been identified. Transgenes inserted into these sites would not result in the inactivation of a gene essential to the survival, vitality, viability, or phenotypic characteristics of the transformed animal or plant.

BRIEF DESCRIPTION OF THE TABLE

Table I provides the tissue specificities of promoters of the invention.

DETAILED DISCLOSURE OF THE INVENTION

The present invention provides polynucleotides which act as regulatory sequences and/or encode useful proteins. The useful proteins encoded by the polynucleotide sequences of the subject invention may, themselves, be involved in the regulation of gene expression.

The isolated polynucleotides of the subject invention are particularly useful in the modification of gene expression in plants. In a particularly preferred embodiment, the polynucleotide sequences of the subject invention are used to modulate gene expression in rice. Specifically exemplified herein are embodiments in which expression in rice roots is targeted. More specifically, this invention relates to plant polynucleotide sequences encoding promoters that are components of the cellular activation and transcription apparatus and the use of such polynucleotide sequences in the modification of expression of endogenous genes. The subject invention also relates to compositions isolated from plants and their use in the modification of gene activation and/or expression.

The polynucleotide sequences disclosed herein are useful in methods including, but not limited to, monitoring the changes of a growth media composition (such as chemical and hormone changes), monitoring of general plant stresses (such as drought, cold, salinity, heat, aerobic, anaerobic, nutritional), plant response to pests and pathogens, and in assays used to characterize and/or identify sequences having as probes regulatory functions (promoters, terminators, enhancers, repressors, etc.).

One method for controlling gene expression according to the subject invention provides materials and methods using double-stranded interfering RNA (dsRNAi), or RNA-mediated interference (RNAi). The terms dsRNAi and RNAi are used interchangeably herein unless otherwise noted. In a more preferred embodiment, the methods and compositions are useful for regulation of gene expression in rice. Thus, in one embodiment of the invention, dsRNAi molecules are provided which are useful in regulating gene expression in plants; the dsRNAi molecules are also useful for the regulation of levels of specific mRNA in plants, particularly rice.

RNA containing a nucleotide sequence identical to a fragment of the target gene is preferred for inhibition; however, RNA sequences with insertions, deletions, and point mutations relative to the target sequence can also be used for inhibition. Sequence identity may optimized by sequence comparison and alignment algorithms known in the art (see Gribskov and Devereux, *Sequence Analysis Primer*, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Alternatively, the duplex region of the RNA may be defined functionally as a nucleotide sequence that is capable of hybridizing with a fragment of the target gene transcript.

As disclosed herein, 100% sequence identity between the RNA and the target gene is not required to practice the present invention. Thus the invention has the advantage of being able to tolerate sequence variations that might be expected due to genetic mutation, strain polymorphism, or evolutionary divergence.

RNA may be synthesized either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the RNA strand (or strands); the promoters may be known inducible promoters that respond to infection, stress, temperature, wounding, or chemicals. Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus. RNA may be chemically or enzymatically synthesized by manual or automated reactions. The RNA may be synthesized by a cellular RNA polymerase or a bacteriophage RNA polymerase (e.g., T3, T7, SP6). The use and production of an expression construct are known in the art (see, for example, WO 97/32016; U.S. Pat. Nos. 5,593,874; 5,698,425; 5,712,135; 5,789,214; and 5,804,693; and the references cited therein). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. The RNA may be dried for storage or dissolved in an aqueous solution. The solution may contain buffers or salts to promote annealing, and/or stabilization of the duplex strands.

Preferably and most conveniently, dsRNAi can be targeted to an entire polynucleotide sequence set forth herein. Preferred RNAi molecules of the instant invention are highly homologous or identical to the polynucleotides of the sequence listing. The homology may be greater than 70%, preferably greater than 80%, more preferably greater than 90% and is most preferably greater than 95%.

Fragments of genes can also be utilized for targeted suppression of gene expression. These fragments are typically in the approximate size range of about 20 nucleotides. Thus, targeted fragments are preferably at least about 15 nucleotides. In certain embodiments, the gene fragment targeted by the RNAi molecule is about 20–25 nucleotides in length. In a more preferred embodiment, the gene fragments are at least about 25 nucleotides in length. In an even more preferred embodiment, the gene fragments are at least 50 nucleotides in length.

Thus, RNAi molecules of the subject invention are not limited to those that are targeted to the full-length polynucleotide or gene. Gene product can be inhibited with a RNAi molecule that is targeted to a portion or fragment of the exemplified polynucleotides; high homology (90–95%) or greater identity is also preferred, but not necessarily essential, for such applications.

In another aspect of the invention, the dsRNA molecules of the invention may be introduced into plant cells with single stranded (ss) RNA molecules which are sense or anti-sense RNA derived from the nucleotide sequences disclosed herein. Methods of introducing ssRNA and dsRNA molecules into cells are well-known to the skilled artisan and includes transcription of plasmids, vectors, or genetic constructs encoding the ssRNA or dsRNA molecules according to this aspect of the invention; electroporation, biolistics, or other well-known methods of introducing nucleic acids into plant cells may also be used to introduce the ssRNA and dsRNA molecules of this invention into plant cells.

Advantageously, the subject invention also provides unique polynucleotides which have been identified as novel gene promoters in eucaryotic organisms. These promoters are components of the cellular activation and transcription apparatus and may be tissue, organ, or cell specific. The invention also comprises polynucleotides which are complementary to the disclosed polynucleotide sequences. The invention further comprises the use of the disclosed polynucleotide sequences, or fragments thereof, in assays to characterize and/or identify sequences having promoter or other regulatory activity. Also contemplated according to the subject invention is the use of oligomers from these sequences in kits which can be used to identify promoters.

As a result of the degeneracy of the genetic code, a multitude of nucleotide sequences may be produced which are based upon the sequences provided herein and corresponding peptides, polypeptides, or proteins. Some of these nucleotide sequences will bear only minimal homology to the sequences disclosed herein; however the subject invention specifically contemplates each and every possible variation of nucleotide sequence that could be made by selecting combinations based on possible codon choices. These combinations are made in accordance with the standard triplet genetic code as applied to the nucleotide sequence of naturally occurring peptide, polypeptide, or protein, and all such variations are to be considered as being specifically disclosed herein.

It is possible to produce the polynucleotides of the subject invention, or portions thereof, entirely by synthetic chemistry. After synthesis, the nucleic acid sequence can be used alone or joined with a preexisting sequence and inserted into one of the many available DNA vectors and their respective host cells using techniques well known in the art. Moreover, synthetic chemistry may be used to introduce specific mutations into the nucleotide sequence. Alternatively, a portion of sequence in which a mutation is desired can be synthesized and recombined with a portion of an existing genomic or recombinant sequence.

Nucleotide sequences encoding a peptide, polypeptide, or protein may be joined to a variety of other nucleotide sequences by means of well established recombinant DNA techniques (Sambrook J. et al. (1989) Molecular Cloning: A Laboratory Manual, Cold Spring Harbor Laboratory, Cold Spring Harbor, N.Y.; or Ausubel F. M. et al. (1989) Current Protocols in Molecular Biology, John Wiley & Sons, New York City). Useful sequences include an assortment of cloning vectors such as plasmids, cosmids, lambda phage derivatives, phagemids, and the like. Vectors of interest include vectors for replication, expression, probe generation, sequencing, and the like. In general, vectors of interest may contain an origin of replication functional in at least one organism, convenient restriction endonuclease sensitive sites, and selectable markers for one or more host cell systems.

Another aspect of the subject invention is to provide for hybridization probes which are capable of hybridizing with naturally occurring nucleotide promoter sequences or nucleotide sequences encoding the disclosed peptide, polypeptide, or protein. The stringency of the hybridization conditions will determine whether the probe identifies only the native nucleotide sequence or sequences of closely related molecules. If degenerate nucleotide sequences of the subject invention are used for the detection of related sequences, they should preferably contain at least 50% of the nucleotides of the sequences presented herein.

Hybridization probes of the subject invention may be derived from the nucleotide sequences of the attached List Sequences, or from surrounding or included genomic sequences comprising untranslated regions such as promoters, enhancers and introns. Such hybridization probes may be labeled with appropriate reporter molecules. Means for producing specific hybridization probes include oligolabelling, nick translation, end-labeling or PCR amplification using a labeled nucleotide. Alternatively, the cDNA sequence may be cloned into a vector for the production of mRNA probe. Such vectors are known in the art, are commercially available, and may be used to synthesize RNA probes in vitro by addition of an appropriate RNA polymerase such as T7, T3 or SP6 and labelled nucleotides. A number of companies (such as Pharmacia Biotech, Piscataway, N.J.; Promega, Madison, Wis.; US Biochemical Corp, Cleveland, Ohio; etc.) supply commercial kits and protocols for these procedures.

The nucleotide sequences (shown in the List Sequences) can be used to generate probes for mapping the native genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes (YACs), bacterial artificial chromosomes (BACs), bacterial PI constructions or single chromosome CDNA libraries.

In situ hybridization of chromosomal preparations and physical mapping techniques such as linkage analysis using established chromosomal markers are invaluable in extending genetic maps. The nucleotide sequences of the subject invention may also be used to detect differences in the chromosomal location of nucleotide sequences due to translocation, inversion, or recombination.

Other aspects of the invention include use of the disclosed sequences or recombinant nucleic acids derived therefrom to produce purified peptides. The nucleotide sequences as disclosed herein may be used to produce an amino acid sequence using well known methods of recombinant DNA technology. Goeddel (Gene Expression Technology, Methods and Enzymology [1990] Vol 185, Academic Press, San Diego, Calif.) is one among many publications which teach expression of an isolated, purified nucleotide sequence. The amino acid or peptide may be expressed in a variety of host cells, either prokaryotic or eukaryotic. Host cells may be from the same species from which the nucleotide sequence was derived or from a different species.

Still further aspects of the invention use these purified peptides to produce antibodies or other molecules able to bind to the peptides. These antibodies or binding agents can then be used for the screening of cells in order to localize the cellular distribution of the peptides or proteins. The antibodies are also useful for the affinity purification of recombinantly produced peptides or proteins.

The disclosed nucleotide sequences can be used individually, or in panels, in tests or assays to detect levels of peptide, polypeptide, or protein expression. The form of such qualitative or quantitative methods may include northern analysis, dot blot or other membrane based technologies, dip stick, pin or chip technologies, PCR, ELISAs or other multiple sample format technologies.

As used herein, the following definitions apply:

An "oligonucleotide" or "oligomer" is a stretch of nucleotide residues which has a sufficient number of bases to be used in a polymerase chain reaction (PCR). These short sequences are based on (or designed from) genomic or cDNA sequences and are used to amplify, confirm, or reveal the presence of an identical, similar or complementary DNA or RNA in a particular cell or tissue. Oligonucleotides or oligomers comprise portions of a DNA sequence having at least about 10 nucleotides and as many as about 50 nucleotides, preferably about 15 to 30 nucleotides. They can be chemically synthesized and may be used as probes.

"Probes" are nucleic acid sequences of variable length, preferably between at least about 10 and as many as about 6,000 nucleotides, depending on use. They are used in the detection of identical, similar, or complementary nucleic acid sequences. Longer length probes are usually obtained from a natural or recombinant source, are highly specific and much slower to hybridize than oligomers. They may be single- or double-stranded and designed to have specificity in PCR, hybridization membrane-based, or ELISA-like technologies.

"Reporter" molecules are chemical moieties used for labeling a nucleic or amino acid sequence. They include, but are not limited to, radionuclides, enzymes, fluorescent, chemi-luminescent, or chromogenic agents. Reporter molecules associate with, establish the presence of, and may allow quantification of a particular nucleic or amino acid sequence.

A "portion" or "fragment" of a polynucleotide or nucleic acid comprises all or any part of the nucleotide sequence having fewer nucleotides than about 6 kb, preferably fewer than about 1 kb which can be used as a probe. Such probes may be labeled with reporter molecules using nick translation, Klenow fill-in reaction, PCR or other methods well known in the art. After pretesting to optimize reaction conditions and to eliminate false positives, nucleic acid probes may be used in Southern, northern or in situ hybridizations to determine whether target DNA or RNA is present in a biological sample, cell type, tissue, organ or organism.

"Recombinant nucleotide variants" are alternate polynucleotides which encode a particular protein. They may be synthesized, for example, by making use of the "redundancy" in the genetic code. Various codon substitutions, such as the silent changes which produce specific restriction sites or codon usage-specific mutations, may be introduced to optimize cloning into a plasmid or viral vector or expression in a particular prokaryotic or eukaryotic host system, respectively.

"Linkers" are synthesized palindromic nucleotide sequences which create internal restriction endonuclease sites for ease of cloning the genetic material of choice into various vectors. "Polylinkers" are engineered to include multiple restriction enzyme sites and provide for the use of both those enzymes which leave 5' and 3' overhangs such as BamHI, EcoRI, PstI, Kpnl and Hind III or which provide a blunt end such as EcoRV, SnaBI and StuI.

"Control elements" or "regulatory sequences" are regions of the gene or DNA such as enhancers, promoters, introns and 3' untranslated regions which interact with cellular proteins to carry out replication, transcription, and translation. Typically, these regions are nontranslated. They may occur as boundary sequences or even split the gene. They function at the molecular level and along with regulatory genes are very important in development, growth, differentiation and aging processes.

"Chimeric" molecules are polynucleotides or polypeptides which are created by combining one or more nucleotide peptide sequences (or their parts). In the case of nucleotide sequences, such combined sequences may be introduced into an appropriate vector and expressed to give rise to a chimeric polypeptide which may be expected to be different from the native molecule in one or more of the following characteristics: cellular location, distribution, ligand-binding affinities, interchain affinities, degradation/turnover rate, signaling, etc.

"Active" is that state which is capable of being useful or of carrying out some role. It specifically refers to those forms, fragments, or domains of an amino acid sequence which display the biologic and/or immunogenic activity characteristic of the naturally occurring peptide, polypeptide, or protein.

"Naturally occurring" refers to a polypeptide produced by cells which have not been genetically engineered or which have been genetically engineered to produce the same sequence as that naturally produced.

"Derivative" refers to those polypeptides which have been chemically modified by such techniques as ubiquitination, labeling, pegylation (derivatization with polyethylene glycol), and chemical insertion or substitution of amino acids such as ornithine which do not normally occur in proteins.

"Recombinant polypeptide variant" refers to any polypeptide which differs from naturally occurring peptide, polypeptide, or protein by amino acid insertions, deletions and/or substitutions.

Amino acid "substitutions" are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid "insertions" or "deletions" are changes to or within an amino acid sequence. They typically fall in the range of about 1 to 5 amino acids. The variation allowed in a particular amino acid sequence may be experimentally determined by producing the peptide synthetically or by systematically making insertions, deletions, or substitutions of nucleotides in the sequence using recombinant DNA techniques.

A "signal or leader sequence" is a short amino acid sequence which can be used, when desired, to direct the polypeptide through a membrane of a cell. Such a sequence may be naturally present on the polypeptides of the present invention or provided from heterologous sources by recombinant DNA techniques. Such sequences include nuclear localization sequences (NLS) known in the art.

An "oligopeptide" is a short stretch of amino acid residues and may be expressed from an oligonucleotide. Such sequences comprise a stretch of amino acid residues of at least about 5 amino acids and often about 17 or more amino acids, typically at least about 9 to 13 amino acids, and of sufficient length to display biologic and/or immunogenic activity.

An "inhibitor" is a substance which retards or prevents a chemical or physiological reaction or response. Common inhibitors include but are not limited to antisense molecules, antibodies, antagonists and their derivatives.

A "standard" is a quantitative or qualitative measurement for comparison. Preferably, it is based on a statistically appropriate number of samples and is created to use as a basis of comparison when performing diagnostic assays, running clinical trials, or following patient treatment profiles. The samples of a particular standard may be normal or similarly abnormal.

Since the list of technical and scientific terms cannot be all encompassing, any undefined terms shall be construed to have the same meaning as is commonly understood by one of skill in the art to which this invention belongs. Furthermore, the singular forms "a", "an" and "the" include plural referents unless the context clearly dictates otherwise.

The invention is not to be limited only to the particular sequences, variants, formulations or methods described. The sequences, variants, formulations and methodologies may vary, and the terminology used herein is for the purpose of describing particular embodiments. The terminology and definitions are not intended to be limiting.

Polynucleotide Probes. DNA possesses a fundamental property called base complementarity. In nature, DNA ordinarily exists in the form of pairs of anti-parallel strands, the bases on each strand projecting from that strand toward the opposite strand. The base adenine (A) on one strand will always be opposed to the base thymine (T) on the other strand, and the base guanine (G) will be opposed to the base cytosine (C). The bases are held in apposition by their ability to hydrogen bond in this specific way. Though each individual bond is relatively weak, the net effect of many adjacent hydrogen bonded bases, together with base stacking effects, is a stable joining of the two complementary strands. These bonds can be broken by treatments such as high pH or high temperature, and these conditions result in the dissociation, or "denaturation," of the two strands. If the DNA is then placed in conditions which make hydrogen bonding of the bases thermodynamically favorable, the DNA strands will anneal, or "hybridize," and reform the original double- stranded DNA. If carried out under appropriate conditions, this hybridization can be highly specific. That is, only strands with a high degree of base complementarity will be able to form stable double-stranded structures. The relationship of the specificity of hybridization to reaction conditions is well known. Thus, hybridization may be used to test whether two pieces of DNA are complementary in their base sequences. It is this hybridization mechanism which facilitates the use of probes of the subject invention to readily detect and characterize DNA sequences of interest.

The specifically exemplified polynucleotides of the subject invention can themselves be used as probes. Additional polynucleotide sequences can be added to the ends of (or internally in) the exemplified polynucleotide sequences so that polynucleotides that are longer than the exemplified polynucleotides can also be used as probes. Thus, isolated polynucleotides comprising one or more of the exemplified sequences are within the scope of the subject invention. Polynucleotides that have less nucleotides than the exemplified polynucleotides can also be used and are contemplated within the scope of the present invention. For example, for some purposes, it might be useful to use a conserved sequence from an exemplified polynucleotide wherein the conserved sequence comprises a portion of an exemplified sequence. Thus, polynucleotides of the subject invention can be used to find additional, homologous (wholly or partially) genes.

Probes of the subject invention may be composed of DNA, RNA, or PNA (peptide nucleic acid). The probe will normally have at least about 10 bases, more usually at least about 17 bases, and may have up to about 100 bases or more. Longer probes can readily be utilized, and such probes can be, for example, several kilobases in length. The probe sequence is designed to be at least substantially complementary to a portion of a gene encoding a protein of interest. The probe need not have perfect complementarity to the sequence to which it hybridizes. The probes may be labeled utilizing techniques that are well known to those skilled in this art.

One approach for the use of the subject invention as probes entails first identifying DNA segments that are homologous with the disclosed nucleotide sequences using, for example, Southern blot analysis of a gene bank. Thus, it is possible, without the aid of biological analysis, to know in advance the probable activity of many new polynucleotides, and of the individual gene products expressed by a given polynucleotide. Such an analysis provides a rapid method for identifying commercially valuable compositions.

One hybridization procedure useful according to the subject invention typically includes the initial steps of isolating the DNA sample of interest and purifying it chemically. Either lysed cells or total fractionated nucleic acid isolated from cells can be used. Cells can be treated using known techniques to liberate their DNA (and/or RNA). The DNA sample can be cut into pieces with an appropriate restriction enzyme. The pieces can be separated by size through electrophoresis in a gel, usually agarose or acrylamide. The pieces of interest can be transferred to an immobilizing membrane.

The particular hybridization technique is not essential to the subject invention. As improvements are made in hybridization techniques, they can be readily applied.

The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. As is well known in the art, if the probe molecule and nucleic acid sample hybridize by forming a strong non-covalent bond between the two molecules, it can be reasonably assumed that the probe and sample are essentially identical or very similar. The probe's detectable label provides a means for determining in a known manner whether hybridization has occurred.

In the use of the nucleotide segments as probes, the particular probe is labeled with any suitable label known to those skilled in the art, including radioactive and non-radioactive labels. Typical radioactive labels include $^{32}$P, $^{35}$S, or the like. Non-radioactive labels include, for example, ligands such as biotin or thyroxine, as well as enzymes such as hydrolases or peroxidases, or the various chemiluminescers such as luciferin, or fluorescent compounds like fluorescein and its derivatives. In addition, the probes can be made inherently fluorescent as described in International Application No. WO 93/16094.

Various degrees of stringency of hybridization can be employed. The more stringent the conditions, the greater the complementarity that is required for duplex formation. Stringency can be controlled by temperature, probe concentration, probe length, ionic strength, time, and the like. Preferably, hybridization is conducted under moderate to high stringency conditions by techniques well known in the art, as described, for example, in Keller, G. H., M. M. Manak (1987) *DNA Probes*, Stockton Press, New York, N.Y., pp. 169–170.

As used herein "moderate to high stringency" conditions for hybridization refers to conditions that achieve the same, or about the same, degree of specificity of hybridization as the conditions "as described herein." Examples of moderate to high stringency conditions are provided herein. Specifically, hybridization of immobilized DNA on Southern blots with $^{32}$P-labeled gene-specific probes was performed using standard methods (Maniatis et al.). In general, hybridization and subsequent washes were carried out under moderate to high stringency conditions that allowed for detection of target sequences with homology to sequences exemplified herein. For double-stranded DNA gene probes, hybridization was carried out overnight at 20–25° C. below the melting temperature (Tm) of the DNA hybrid in 6×SSPE, 5×Denhardt's solution, 0.1% SDS, 0.1 mg/ml denatured DNA. The melting temperature is described by the following formula from Beltz et al. (1983):

Tm=81.5° C.+16.6 Log[Na+]+0.41 (%G+C)−0.61 (%formamide)−600/length duplex in base pairs.

Washes are typically carried out as follows:
(1) Twice at room temperature for 15 minutes in 1×SSPE, 0.1% SDS (low stringency wash).
(2) Once at Tm−20° C. for 15 minutes in 0.2×SSPE, 0.1% SDS (moderate stringency wash).

For oligonucleotide probes, hybridization was carried out overnight at 10–20° C. below the melting temperature (Tm) of the hybrid in 6×SSPE, 5×Denhardt's solution, 0.1% SDS, 0.1 mg/ml denatured DNA. Tm for oligonucleotide probes was determined by the following formula from Suggs et al. (1981):

Tm (° C.)=2(number T/A base pairs)+4(number G/C base pairs)

Washes were typically carried out as follows:
(1) Twice at room temperature for 15 minutes 1×SSPE, 0.1% SDS (low stringency wash).
(2) Once at the hybridization temperature for 15 minutes in 1×SSPE, 0.1% SDS (moderate stringency wash).

In general, salt and/or temperature can be altered to change stringency. With a labeled DNA fragment of greater than about 70 or so bases in length, the following conditions can be used:

Low: 1 or 2×SSPE, room temperature
Low: 1 or 2×SSPE, 42° C.
Moderate: 0.2×or 1×SSPE, 65° C.
High: 0.1×SSPE, 65° C.

Duplex formation and stability depend on substantial complementarity between the two strands of a hybrid, and, as noted above, a certain degree of mismatch can be tolerated. Therefore, polynucleotide sequences of the subject invention include mutations (both single and multiple), deletions, and insertions in the described sequences, and combinations thereof, wherein said mutations, insertions, and deletions permit formation of stable hybrids with a target polynucleotide of interest. Mutations, insertions, and deletions can be produced in a given polynucleotide sequence using standard methods known in the art. Other methods may become known in the future.

The mutational, insertional, and deletional variants of the polypeptide sequences of the invention can be used in the same manner as the exemplified polynucleotide sequences so long as the variants have substantial sequence similarity with the original sequence. As used herein, substantial sequence similarity refers to the extent of nucleotide similarity that is sufficient to enable the variant polynucleotide to function in the same capacity as the original sequence. Preferably, this similarity is greater than 50%; more preferably, this similarity is greater than 75%; and most preferably, this similarity is greater than 90%. The degree of similarity needed for the variant to function in its intended capacity will depend upon the intended use of the sequence. It is well within the skill of a person trained in this art to make mutational, insertional, and deletional mutations that are designed to improve the function of the sequence or otherwise provide a methodological advantage.

PCR Technology. Polymerase Chain Reaction (PCR) is a repetitive, enzymatic, primed synthesis of a nucleic acid sequence. This procedure is well known and commonly used by those skilled in this art (see U.S. Pat. Nos. 4,683,195, 4,683,202, and 4,800,159; Saiki et al., 1985). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase, which is isolated from the thermophilic bacterium *Thermus aquaticus*, the amplification process can be completely automated. Other enzymes that can be used are known to those skilled in the art.

The polynucleotide sequences of the subject invention (and portions thereof such as conserved regions and portions that serve to distinguish these sequences from previously-known sequences) can be used as, and/or used in the design of, primers for PCR amplification. In performing PCR amplification, a certain degree of mismatch can be tolerated between primer and template. Therefore, mutations, deletions, and insertions (especially additions of nucleotides to the 5' end) of the exemplified ppolynucleotides can be used in this manner. Mutations, inpsertions and deletions can be produced in a given primer by methods known to an ordinarily skilled artisan.

Full length genes may be cloned utilizing partial nucleotide sequence and various methods known in the art. Gobinda et al. (1993; *PCR Methods Applic* 2:318–22) disclose "restriction-site PCR" as a direct method which uses universal primers to retrieve unknown sequence adjacent to a known locus. First, genomic DNA is amplified in the presence of primer to linker and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to acquire unknown sequences starting with primers based on a known region (Triglia T. et al. (1988) *Nucleic Acids Res* 16:8186). The method uses several restriction enzymes to generate a suitable fragment in the known region of a gene. The fragment is then circularized by intramolecular ligation and used as a PCR template. Divergent primers are designed from the known region. The multiple rounds of restriction enzyme digestions and ligations that are necessary prior to PCR make the procedure slow and expensive (Gobinda et al. [1993] supra).

Capture PCR (Lagerstrom M. et al. (1991) *PCR Methods Applic* 1:111–19) is a method for PCR amplification of DNA fragments adjacent to a known sequence in eucaryotic and YAC DNA. As noted by Gobinda et al. (1993,supra), capture PCR also requires multiple restriction enzyme digestions and ligations to place an engineered double-stranded sequence into an unknown portion of the DNA molecule before PCR. Although the restriction and ligation reactions are carried out simultaneously, the requirements for extension, immobilization and two rounds of PCR and purification prior to sequencing render the method cumbersome and time consuming.

Parker J. D. et al. (*Nucleic Acids Res* [1991]19:3055–60), teach walking PCR, a method for targeted gene walking which permits retrieval of unknown sequences. Promoter-Finder™ is a kit available from Clontech Laboratories, Inc. (Palo Alto, Calif.) which uses PCR and primers derived from p53 to walk in genomic DNA. Nested primers and special PromoterFinder™ libraries are used to detect upstream sequences such as promoters and regulatory elements. This process avoids the need to screen libraries and is useful in finding intron/exon junctions.

A new PCR method replaces methods which use labeled probes to screen plasmid libraries and allow one researcher to process only about 3–5 genes in 14–40 days. In the first step, which can be performed in about two days, any two of a plurality of primers are designed and synthesized based on a known partial sequence. In step 2, which takes about six to eight hours, the sequence is extended by PCR amplification of a selected library. Steps 3 and 4, which take about one day, are purification of the amplified cDNA and its ligation into an appropriate vector. Step 5, which takes about one day, involves transforming and growing up host bacteria. In step 6, which takes approximately five hours, PCR is used to screen bacterial clones for extended sequence. The final steps, which take about one day, involve the preparation and sequencing of selected clones.

If the full length cDNA has not been obtained, the entire procedure is repeated using either the original library or some other preferred library. The preferred library may be one that has been size-selected to include only larger cDNAs or may consist of single or combined commercially available libraries, e.g., from Clontech Laboratories, Inc. (Palo Alto, Calif.). The cDNA library may have been prepared with oligo (dT) or random priming. Random primed libraries are preferred in that they will contain more sequences which contain 5' ends of genes. A randomly primed library may be particularly useful if an oligo (dT) library does not yield a complete gene. It must be noted that the larger and more complex the protein, the less likely it is that the complete gene will be found in a single plasmid.

CLONTECH PCR-Select™ cDNA Subtraction (Clontech Laboratories, Inc., Palo Alto, Calif.) is yet another means by which differentially expressed genes may be isolated. The procedure allows for the isolation of transcripts present in one mRNA population which is absent, or found in reduced numbers, in a second population of mRNA. Rare transcripts may be enriched 1000-fold.

A new method for analyzing either the size or the nucleotide sequence of PCR products is capillary electrophoresis. Systems for rapid sequencing are available from Perkin Elmer (Foster City Calif.), Beckman Instruments (Fullerton, Calif.), and other companies. Capillary sequencing employs flowable polymers for electrophoretic separation, four different fluorescent dyes (one for each nucleotide) which are laser activated, and detection of the emitted wavelengths by a charge coupled devise camera. Output/light intensity is converted to electrical signal using appropriate software (eg. Genotyper™ and Sequence Navigators™ from Perkin Elmer) and the entire process from loading of samples to computer analysis and electronic data display is computer controlled. Capillary electrophoresis provides greater resolution and is many times faster than standard gel based procedures. It is particularly suited to the sequencing of small pieces of DNA which might be present in limited amounts in a particular sample. The reproducible sequencing of up to 350 bp of M13 phage DNA in 30 min has been reported (Ruiz-Martinez M. C. et al. [1993] *Anal Chem* 65:2851–8).

Polynucleotides and Proteins. Polynucleotides of the subject invention can be defined according to several parameters. One characteristic is the biological activity of the protein products as identified herein. The proteins and genes of the subject invention can be further defined by their amino acid and nucleotide sequences. The sequences of the molecules can be defined in terms of homology to certain exemplified sequences as well as in terms of the ability to hybridize with, or be amplified by, certain exemplified probes and primers. Additional primers and probes can readily be constructed by those skilled in the art such that alternate polynucleotide sequences encoding the same amino acid sequences can be used to identify and/or characterize additional genes. The proteins of the subject invention can also be identified based on their immunoreactivity with certain antibodies.

The polynucleotides and proteins of the subject invention include portions, fragments, variants, and mutants of the full-length sequences as well as fusions and chimerics, so long as the encoded protein retains the characteristic biological activity of the proteins identified herein. As used herein, the terms "variants" or "variations" of genes refer to nucleotide sequences that encode the same proteins or which encode equivalent proteins having equivalent biological activity. As used herein, the term "equivalent proteins" refers to proteins having the same or essentially the same biological activity as the exemplified proteins.

Variations of genes may be readily constructed using standard techniques such as site-directed mutagenesis and other methods of making point mutations and by DNA shuffling, for example. In addition, gene and protein fragments can be made using commercially available exonucleases, endonucleases, and proteases according to standard procedures. For example, enzymes such as Bal31 can be used to systematically cut off nucleotides from the ends of genes. Also, genes that encode fragments may be obtained using a variety of restriction enzymes. Proteases may be used to directly obtain active fragments of these proteins. Of course, molecular techniques for cloning polynucleotides and producing gene constructs of interest are also well known in the art. In vitro evaluation techniques, such as MAXYGEN's "Molecular Breeding" can also be applied to practice the subject invention.

Because of the redundancy of the genetic code, a variety of different DNA sequences can encode the amino acid sequences encoded by the polynucleotide sequences disclosed herein. It is well within the skill of a person trained in the art to create these alternative DNA sequences encoding proteins having the same, or essentially the same, amino acid sequence. These variant DNA sequences are within the scope of the subject invention. As used herein, reference to "essentially the same" sequence refers to sequences that have amino acid substitutions, deletions, additions, or insertions that do not materially affect biological activity. Fragments retaining the characteristic biological activity are also included in this definition.

A further method for identifying genes and polynucleotides (and the proteins encoded thereby) of the subject invention is through the use of oligonucleotide probes. Probes provide a rapid method for identifying genes of the subject invention. The nucleotide segments that are used as probes according to the invention can be synthesized using a DNA synthesizer and standard procedures.

The subject invention comprises variant or equivalent proteins (and nucleotide sequences coding for equivalent proteins) having the same or similar biological activity of proteins encoded by the exemplified polynucleotides. Equivalent proteins will have amino acid similarity with an exemplified protein (or peptide). The amino acid identity will typically be greater than 60%. Preferably, the amino acid identity will be greater than 75%. More preferably, the amino acid identity will be greater than 80%, and even more preferably greater than 90%. Most preferably, amino acid identity will be greater than 95%. (Likewise, the polynucleotides that encode the subject polypeptides will also have corresponding identities in these preferred ranges.) These identities are as determined using standard alignment techniques for determining amino acid identity. The amino acid identity/similarity/ homology will be highest in critical regions of the protein including those regions that account for biological activity or that are involved in the determination of three-dimensional configuration that is ultimately responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Below is a list of examples of amino acids belonging to various classes.

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made.

As used herein, reference to "isolated" polynucleotides and/or "purified" proteins refers to these molecules when they are not associated with the other molecules with which they would be found in nature. Thus, reference to "isolated" and/or "purified" signifies the involvement of the "hand of man" as described herein. Reference to "heterologous" proteins, genes, and gene constructs, also signifies the involvement of the "hand of man."

Recombinant Hosts. The genes and polynucleotides within the scope of the present invention can be introduced into a wide variety of microbial or plant hosts.

There are many methods for introducing a heterologous gene or polynucleotide into a host cell or cells under conditions that allow for stable maintenance and expression of the gene or polynucleotide. These methods are well known to those skilled in the art. Synthetic genes, such as, for example, those genes modified to enhance expression in a heterologous host (such as by preferred codon usage or by the use of adjoining, downstream, or upstream enhancers)

that are functionally equivalent to the genes (and which encode equivalent proteins) can also be used to transfect hosts. Methods for the production of synthetic genes are known in the art.

Antibody Production

Although an amino acid sequence or oligopeptide used for antibody induction does not require biological activity, it must be immunogenic. A peptide, polypeptide, or protein used to induce specific antibodies may have an amino acid sequence consisting of at least five amino acids and preferably at least 10 amino acids. Short stretches of amino acid sequence may be genetically or chemically fused with those of another protein such as keyhole limpet hemocyanin, and the chimeric peptide used for antibody production. Alternatively, the oligopeptide may be of sufficient length to contain an entire domain.

Antibodies specific for peptides, polypeptides, or proteins may be produced by inoculation of an appropriate animal with an antigenic fragment of the peptide, polypeptide, or protein. Antibody production includes not only the stimulation of an immune response by injection into animals, but also analogous processes such as the production of synthetic antibodies, the screening of recombinant immunoglobulin libraries for specific-binding molecules (Orlandi R. et al. [1989] *PNAS* 86:3833–3837, or Huse W. D. et al. [1989] *Science* 256:1275–1281), or the in vitro stimulation of lymphocyte populations. Current technology (Winter G. and Milstein C. [1991] *Nature* 349:293–299) provides for a number of highly specific binding reagents based on the principles of antibody formation. These techniques may be adapted to produce molecules which specifically bind kinase peptides. Antibodies or other appropriate molecules generated against a specific immunogenic peptide fragment or oligopeptide can be used in Western analysis, enzyme-linked immunosorbent assays (ELISA) or similar tests to establish the presence of or to quantitate amounts of peptide, polypeptide, or protein in normal, diseased, or transformed cells, tissues, organs, or organisms as well as liquid suspensions containing said peptide, polypeptide, or protein.

Following are examples which illustrate procedures for practicing the invention. These examples should not be construed as limiting. All percentages are by weight and all solvent mixture proportions are by volume unless otherwise noted.

EXAMPLE 1

Identification of Rice Polynucleotide Sequences

Polynucleotide sequences encoding proteins were isolated by PCR-Select™ cDNA Subtraction (Clontech Laboratories, Inc., Palo Alto, Calif.). First, mRNA populations from rice genomic libraries (Clontech Laboratories, Inc.) of roots and shoots were converted into cDNA. We named rice cDNA that contains specific (differentially expressed) transcripts as "tester" (roots), and the reference cDNA as "driver" (shoots). Tester and driver cDNA are hybridized, and the hybrid sequences are then removed. Consequently, the remaining unhybridized cDNAs represent genes that are expressed in the tester, but are absent from the driver mRNA.

The cDNA synthesized from 2 μg of poly A+RNA from rice roots and shoots were used as tester and driver. Clontech Laboratories PCR-Select™ subtractive library protocol was used to obtain the rice root specific cDNA library. After the subtracted cDNA was obtained, sequencing was performed. The function of the cDNA was deduced by DNA sequence similarity searches in public and proprietary databases as well as by analysis of the expression of these genes under normal and abnormal growth and development conditions. Tissue specificity of the cDNA has been confirmed using the cDNA micro array technique.

EXAMPLE 2

Sequences Identified in Accordance with the Subject Invention are Shown in the Attached List Sequences A further aspect of the subject invention pertains to several promoter sequences from the rice. They are:
1) Tubulin-like rice root specific promoter (root)
2) Anther specific promoter from rice (flower)
3) Rice promoter for Cinnamyl:CoA reductase (Xylem)
4) Rice promoter from Hydroxycinnamte:CoA ligase (Xylem)
5) Rice 16S RNA promoter (constitutive)

EXAMPLE 3

Insertion of Genes Into Plants

One aspect of the subject invention is the transformation of plants with the subject polynucleotide sequences.

Obviously, a promoter region capable of expressing the gene in a plant is needed. Thus, for inplanta expression, the DNA of the subject invention is under the control of an appropriate promoter region. Techniques for obtaining in planta expression by using such constructs is known in the art.

Genes can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC 184, etc. Accordingly, the polynucleotide sequence can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids.

Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters et al. [1978] *Mol. Gen. Genet.* 163:181–187). The Agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

TABLE I

Promoter Tissue Specificity

| Promoter | Internal Identifier | SEQ ID No: | Tissue Specificity | Plant Tested |
|---|---|---|---|---|
| Rice Tubulin | Rice Tubulin | 2 | Root | Arabidopsis |
| 4-CL | 4-CL | 3 | Xylem | Arabidopsis |
| CCR1 | CCR1 | 4 | Xylem | Arabidopsis |
| GAPDH (full sequence) | GAPDH L5-4_11-10-00 | 5 | Constitutive | Rice calli |
| EF-1 α | PGEM EF-1_L3-1-00-11-9-00 | 6 | Constitutive | Rice calli |
| RecA | RecA | 7 | Floral | Arabidopsis |
| 16S | 16S | 8 | Constitutive | Rice calli |
| Anther | Rice Flower (Anther) | 9 | Floral | Arabidopsis |
| Rice Root | Rice Root | 10 | NT | NT |
| B5F9 | EST B5F9 | 11 | Shoots/leaf | Arabidopsis |

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. An isolated polynucleotide sequence comprising SEQ ID NO:1.

2. The polynucleotide sequence of claim 1, wherein said polynucleotide is a promoter.

3. The polynucleotide sequence according to claim 1, wherein said polynucleotide is a tissue specific promoter.

4. A vector comprising an isolated polynucleotide sequence comprising SEQ ID NO:1.

5. The vector according to claim 4, wherein said vector comprises an isolated polynucleotide sequence comprising SEQ ID NO:1 operably linked to a polynucleotide encoding a polypeptide of interest.

6. The vector according to claim 5, further comprising additional regulatory elements.

7. The vector according to claim 4, further comprising polynucleotide sequences encoding one or more selectable marker proteins or polypeptides.

* * * * *

SEQUENCE LISTING

```
<160> NUMBER OF SEQ ID NOS: 12

<210> SEQ ID NO 1
<211> LENGTH: 482
<212> TYPE: DNA
<213> ORGANISM: Oryza sativa
<220> FEATURE:
<221> NAME/KEY: misc_feature
<222> LOCATION: (1)..(482)
<223> OTHER INFORMATION: n = a, c, g, or t.

<400> SEQUENCE: 1
caacgcgttg ggagctctcc catatggtcg acctgcaggc ggccgcgaat tcactagtga      60
ttaagcagtg gtaacaacgc agagtacgcg ggggagaatg tgtttgttat agatcaattc     120
accaatcctg ctaatcctga tgcgcacttc agatggacag gacctgaaat atggaaagat     180
acagcaggca aagtggatat atttgtagct gcatctggtt caggaggcac agtgacaggc     240
```

```
gtagggaggt atctcaagat gaagaatcca tccataaagc tgatatgtgt tgaaccagct    300
gaaagtgcag taatttcagg aggtgaacca gcattccata acatccaagg cataggtcca    360
ggatttatcc cagaaatatt ggacagatca caaatagatg agatagtaac agtgacctct    420
caacacacaa ctaagaaaca tagctaggta accagggaag gtagcatcag cagcgggagg    480
ca                                                                   482
```

<210> SEQ ID NO 2
<211> LENGTH: 938
<212> TYPE: DNA
<213> ORGANISM: Oryza sativa
<220> FEATURE:
<221> NAME/KEY: misc_feature
<222> LOCATION: (1)..(938)
<223> OTHER INFORMATION: n = a, c, g, or t.

<400> SEQUENCE: 2

```
acagtattag tagcaagtca gccacatggg acatggccca catgcatgca cgtcgtatga     60 acacaccgt gattctttgc cacttgcata atattctagc actgctatac tacacgacga    120
ctgacggcga cgtcagttca gttcagtttg ccgcatccat cgcgaaggct actctaccca    180
tcccattttt ttttaaaaaa aaatactata aatctaaata tcttacttta gatttgtata    240
ttttaaagca aagagaataa tatgtagata taagtatgta cctactcgct cgagcacaag    300
atcactgcaa caagcattga agatcgctcc tagcaatggt ctcaacttac catgtaaact    360
aagagcaact ataatgtttt tctttatta ggaatggttg catcttatat tttgagattg     420
agaaaacaca tatagaaatt atacaggatt tagcatttgg gatgccggcc cggattcctg    480
ganttnccca gtctctggct ttcttttaa acaaaaacga aaaaagcagt gatccgatcg    540
atcacgatga gcgagctagt aagctccaaa acaaaataga gtacgtacgt ataatcctag    600
agtccggata ataataatcc gtttggttcg cgttaaaaaa gtcttatctc ctcgtgatcc    660
ctttttttgg atcgatccat gttcgtagta cgtgacaagc acgcgcacca accgaagcag    720
gtacctgtgt cgctgcctgt gggccccaca caccccaaga cggccattaa taaacaaaca    780
cgacgtggcg aagagaaggg aggccggcaa gaagcatact agcacgctac gaaacccccc    840
ttctcttcgt ccccaaattg cactacaaaa aaggccgccc ctttcttctc tcctcgtcct    900
tatcaccacc aatccgatcc tcttctcttc tcttctct                            938
```

<210> SEQ ID NO 3
<211> LENGTH: 1235
<212> TYPE: DNA
<213> ORGANISM: Oryza sativa
<220> FEATURE:
<221> NAME/KEY: misc_feature
<222> LOCATION: (1)..(1235)
<223> OTHER INFORMATION: n = a, c, g, or t.

<400> SEQUENCE: 3

```
ctgcagaaac tactggtgag acggctgggc tggcatagtg gcatggcatc tctctgtgat     60
tgatgtaaat atggacattt tccttgtgtt tcatgcaagt gtaagattaa ttcctttgtt    120
gtgtatgatc cacaatgtta gatcaattat agtattatac tgttgtgcaa tgaaaacaag    180
actgatgagt tatataaatg atggtaaata tgcatttcga gtaactagtg caactattgt    240
tattgatatt tgaaagagat ttttcatgat ttagtaatta tttgtggtta acaagtacta    300
tcaagttgta taatctcccg gaagatgcat gtttccttgc ccaaatacaa tccaaataat    360
```

-continued

| | | |
|---|---|---|
| catgaaagaa agtaaaaaaa aatgacaaca ctcatgcaaa aacgtacata tatcatttta | 420 | |
| caaattctca actataaatt caactcatat atccgaaatt aaaaaagaaa aatcaatttt | 480 | |
| tcataaaata ttgatactat ttatgctcga atttttttaa tgtgtagatc gattttgaac | 540 | |
| atgatttgtg gtgggtggag tgatttatgt cattataata tacattttct ttttttctca | 600 | |
| tattttcatt ataaccattt gcataatatc aagagaacg atcacgaggg acatccctg | 660 | |
| attagaattc cattccttta acaaatcagc attcatcgac acctaatatt cccaaaaaga | 720 | |
| gaagaattaa cgccaaaagn agaacttgat tttctttcag tcctcaatgg attaatacgt | 780 | |
| gggcacattt ttttttttagg tagctagggg ctgcaagagc tagcgagtgt tacgtacgtg | 840 | |
| accgcgtgtg cgcctctcgt ctcgtcttcc tcctcctgct gctgcgttgc tccctacct | 900 | |
| atcccctct ctctccctca tctcgctcct cctgctgcta gctaatgctg tatttattcc | 960 | |
| caccacctcc tcccactctt cgtgcctcgc cggagcaagc agtaccagtg cactgttggt | 1020 | |
| tcgctagcaa gtcggcatta atccgagagt gtgcatgcac cggaggaagc taggtcagct | 1080 | |
| ttgttccggc catgatcacg gtggcggcac cggaggcgca gccgcaggtg gcggcggcgg | 1140 | |
| tcgatgaggc gccgccacag ggggagaaac taatgcagaa caatccgtgc aataacggca | 1200 | |
| tggtagcgat ctggaggcgg tgacggtgtt ccggt | 1235 | |

<210> SEQ ID NO 4
<211> LENGTH: 980
<212> TYPE: DNA
<213> ORGANISM: Oryza sativa
<220> FEATURE:
<221> NAME/KEY: misc_feature
<222> LOCATION: (1)..(980)
<223> OTHER INFORMATION: n = a, c, g, or t.

<400> SEQUENCE: 4

| | | |
|---|---|---|
| actatttagg acaactacaa atgtgtgatg agaacaagga atctagagac aattaatggt | 60 | |
| catacagaca tctgtcaact tcagatggag gtttacaaat agacttgaat aaatgtttat | 120 | |
| ctattttgtg ttggtattat tatttcttgt atagtccttg acgttttta tgctcccgtt | 180 | |
| cagtgaatta tgtaataagt tgctgtaact tgtttgaagc aaagacagaa aatcttttca | 240 | |
| tcatctaaaa aattaaaaata attgacaaga tagattaata tttggtatat cacttccaca | 300 | |
| catgtaaatt caaattaaac tctagctagt atgtgtatat tcacatacat atgagtattt | 360 | |
| tgntttttt ttgcnatata aggatgttaa aattatacct gtatatttaa ttttgggaag | 420 | |
| tgatatatcc ncatattaat tattcttatt aagaactaat ttaaattttt aatagtattt | 480 | |
| tagatggaca tatatncagc aagaaccaag ggaacatctt ctgcaaggat aaaagctttt | 540 | |
| ttttcccca cgatggtgtg ctcttttttt cttgattata accttccggg gtagttttat | 600 | |
| atatccttt tatgccatat ccatatgaaa gatcgcatcg tgcaaattgg acatccttgt | 660 | |
| ggatgtacat agtttatggc caattggaca tccgtgtcct ggtggcattg gacttgaaac | 720 | |
| aaattctgtg gctgcaaatt agaaatgtcc tagtcgatga tgtgtgtaca ttcgtacact | 780 | |
| tcatgtacct ccgtggcgat ggactttgtt gcaacttgca accaaattct gtggctgcgt | 840 | |
| gcgtacgaag gggcttcgat tccaatctga tcagagcggc aaagttcaac cggagatgcc | 900 | |
| gccgcggcgc gtgtgcgtca ccggcgccgg cgggttcatc ggctcgtggc tcgtcaatct | 960 | |
| cctcctctcc tgcggctact | 980 | |

<210> SEQ ID NO 5
<211> LENGTH: 1834

-continued

```
<212> TYPE: DNA
<213> ORGANISM: Oryza sativa
<220> FEATURE:
<221> NAME/KEY: misc_feature
<222> LOCATION: (1)..(1834)
<223> OTHER INFORMATION: n = a, c, g, or t.

<400> SEQUENCE: 5
tggtccttaa ggcccagtaa aatatggacc actcacgtgg gagttctgtt tgggcccaac      60
aggtacttgg ggacgccgtt ccgacccaaa ttggcgtgga gtgcaaaacg gcccgctctt     120
ctgctgcttg ccagaacttc cgcatgatct ctctccagct ctccagccgt ccgagcttct     180
gaagcgctct gctacttgtt ccttgagagt ttgagacgct ttccaccgtc cagccagcat     240
cttgcgctaa tccgctgccg ccgtgaagcc gatccaccga tccacggacc acggccgtct     300
ttttggcttc atgcctccga cccgccttct gctcggacgc ctcctctgcg cgaccatcgg     360
tgcttgatct tttctttttc tttagacaat gataatgatc ggtgcttgat ctgaccatgt     420
attatcttgt cggcgtcaga ttaagcaaac tgcactttca tcttctctgc attttaagca     480
aacggagtat taattaatta atctcggaaa caaaatggta ccaatgggca cggcggtagc     540
catcaactgc cggagatcga aaagangtgg gagaccgaaa atacaactcc gatacaagtc     600
acgggtatcg tcnggcttnt tcgaagaaaa acggacgggc cgccccgccg gacgccgtgc     660
cttttgcgag angaatccga acctgggccc gttgtcatca aaacttgacc naaggangtt     720
aggtaactgt gcccccgtat gtataagttt tggnggggacc ccaattccna atcnaaaagg     780
aatccnttgg ggacggnggn anccattccc aaaaanggga tcnggggggg aaatttcnaa     840
atttgganca ggncaggccc antttnttgn gnaagggnnt tttaataaaa attnttttc      900
ggtnngnaaa aaaggnaaaa ttgcccncna naaaattttt tgccttttca aggggggccg     960
gaaaaccaat ttttgcnaa atggtttggg nttcccncct cccncncct ttttgtttcc     1020
tttcttcccc ccccaaaaa ngccaggntc acctttgccc cacggccctn ttnnttttcc    1080
ttaaagaagg gggcccccaag nggncncggg gcaaaagact tttttaagta actaccaccc    1140
aaacgttcgc ggacccnccn gnnangttcc cngaaatcca ccgcttttcc ggggncccna    1200
cntgtcgcct tgggncngca tgtcatangc gtgcccgcca ccgngntgng ggcgccgcct    1260
ctccccggtg ggtttagaaa ctgtgaggnc gatccgcata cngcggcggc cgtggtgggc    1320
ccaccgtcaa gcgaaaacca ccccgccgc cgcgcgtgcc acgtttactc ccgtgggccc    1380
cgcaacgagg cacaaaccct aggccgctta tataaacccg acccgccccg ctccggtgat    1440
cggatcccca cagctttgcg tttgcactcc tctcgatctc cattcgtttt tgagttcctc    1500
gtttgctccg cctctctttc actcatgggt aaatccgcca atctttgatt ttattttatt    1560
ttgagtttga ttttgggttt gattttgtat gtgttttttgn atgattggtt tgtgatttt    1620
ttttttttgg tttctntgga atgagcaggc aagattaaga tcggaatcaa tggtgagtgt    1680
tcgagcatac gattggatnt ggtnattta tggtatgggg ttnattcggt gcggatttgt    1740
gatggatttt tttggtttgg atgatgcagg gttcggccgc atcggcaggc tggtggccag    1800
ggtggcgctc cagagcgagn atgtngngct cgtc                                1834

<210> SEQ ID NO 6
<211> LENGTH: 965
<212> TYPE: DNA
<213> ORGANISM: Oryza sativa
<220> FEATURE:
<221> NAME/KEY: misc_feature
<222> LOCATION: (1)..(965)
```

<223> OTHER INFORMATION: n = a, c, g, or t.

<400> SEQUENCE: 6

| | | | | | |
|---|---|---|---|---|---|
| aaatatactt | atcacttgag | cgctgcgaaa | cctacagaga | cttgaacgta | acgcaaacgt | 60 |
| ttgaacaggt | cgaccgcagg | attaaaatcg | aacggtcaat | actgccacgc | aacaataacc | 120 |
| accagacaaa | gatcggacgg | ccaggaagga | accctagcac | ccgtggctgc | ctatataaga | 180 |
| ggcaatcctc | tcgccctaac | cccctcctct | ctcccatctc | atcccagccg | ccgccgccgc | 240 |
| agcctcctcc | tctcgccatc | tcccgtcctc | tccttcaagg | tcagcttcag | atcttctcac | 300 |
| ttatccttgt | ttgcgcctgt | tcatgatcgt | tcgtagctgc | agatctggtt | tggtatcgcg | 360 |
| aggtttgggt | gatttggtgc | ttgggcatgt | tgttttcgtt | catttttat | tgtgtattcg | 420 |
| tctcactgct | gtgatcttag | tttgatgtcc | gttgacgcga | agataaactt | gatttgtccg | 480 |
| cgaatcatgt | gcgtatgttg | gaaattatcg | gtagaatcga | acgataaact | tgagttactg | 540 |
| cataatcatc | tacataagtg | gaaaactact | ggtagaatcg | gtagaaaacc | tgtatctaga | 600 |
| atccataatt | tgttgttaaa | ctnctgctga | gtagatgttg | ttattgtccg | tgccctgttc | 660 |
| agttgggtac | tnaaattctg | tatctaaaat | ccaatccgta | aatttgtttc | tgtaaatttg | 720 |
| ttattgtgct | actgctgagt | agatggtgtt | attgtctgta | ccctgttcgg | ttgtgtcgan | 780 |
| tactgcgcgt | ctgtgtaaat | tcatgctga | ttttgatggc | tattaacgtt | ctgtggatgt | 840 |
| ccaagtgatc | tgatctnaga | tcttgcctgt | gatattnatt | tggagttaaa | aattatacag | 900 |
| aaaattgttt | ctaatctntg | ttttattacg | tagaccagtc | agcnacctgc | ttaatcaacc | 960 |
| atggg | | | | | | 965 |

<210> SEQ ID NO 7
<211> LENGTH: 1318
<212> TYPE: DNA
<213> ORGANISM: Oryza sativa
<220> FEATURE:
<221> NAME/KEY: misc_feature
<222> LOCATION: (1)..(1318)
<223> OTHER INFORMATION: n = a, c, g, or t.

<400> SEQUENCE: 7

| | | | | | |
|---|---|---|---|---|---|
| ctgggcacaa | ggtttaacaa | tcaatcaatc | tcgatctttt | ttttgttgat | aatgcaatgg | 60 |
| ctaacctgag | gtatcctttt | ttaatgaaca | gaaggctgga | agaagtcaac | ttgcggaagg | 120 |
| tcaagcaggt | gagaggccac | cggaatgtaa | gcagcagtga | agaagtgaag | aatcttggct | 180 |
| tagttatgat | gaanaagaag | agtgaagagt | gtctttgagc | cgaggttgtg | tttctttaat | 240 |
| ttgcagagtc | atggtccggt | ttattatata | tcaagtttg | ggtgattggt | ttgctattta | 300 |
| aaaaaaaaaa | atgggttctt | tggtttggtt | tgtgtctctt | gattttcct | tttgtaatga | 360 |
| tcttatgaat | ttgnttcgag | ttaatgtcgt | tctctggtca | gatttcgaat | tcaattctat | 420 |
| ntatcctccc | tcgttaatga | gagaatttgt | gaagacaatc | tagtttactt | aagattgatc | 480 |
| gaatttttat | aaaccaacat | taccaaaccc | gtcaaataat | ttnaaaccca | atccaatcnt | 540 |
| atttatcggg | tttgcattaa | ccccatcnat | gagccccgtt | taanccatcc | gttttgaggt | 600 |
| ttctctgggg | aaaganaaaa | gncnaaaacc | ntcttttccc | cccttgnnaa | atnnccaaaa | 660 |
| gccaaaaaca | tctcctnccn | gccttggaaa | angcccgatc | accanaaccc | naaaaaaaat | 720 |
| agttgaaacg | gaggaaacga | aaccctaaac | ccntaaaaac | ctctcctttt | ttttcccagt | 780 |
| aaaatttctc | ttcttctcncn | gttttcatac | aagtctgact | tctggggagt | tggaatttc | 840 |
| cagttttggg | tttgtttctg | tatctgtggt | ttaaaaagt | ggagaagaag | cttttagtg | 900 |

```
cttttctatg gcgaggattc tccgaaacgt ttattcactg agaagctctc tgttttcgtc      960
agaggtatgt ttatcgtgtt tctcatttgg gtattacgag aaattaaaaa aactctgtta     1020
ctgtcgtttt cattgcttat ttgggtattc attcatgaga aagaatccga aatgttgtct     1080
cttaatttga attcattctt ttttctggg taatgtttat tgacaagggt ttcatggggt      1140
tttgcagtta cttagaagaa gtgtggttgg aacatcgttt cagctccgag gctttgctgc     1200
caaaggttgt cttaagcttt tacctttgt ttctatgaat cgattttact caaattggtt      1260
tttgattttg atgaatatat gtatttccac agattactag agctaaatcc gtttgcaa      1318
```

<210> SEQ ID NO 8
<211> LENGTH: 993
<212> TYPE: DNA
<213> ORGANISM: Oryza sativa
<220> FEATURE:
<221> NAME/KEY: misc_feature
<222> LOCATION: (1)..(993)
<223> OTHER INFORMATION: n = a, c, g, or t.

<400> SEQUENCE: 8

```
aaaaactaaa ctacaaaact aggatgaaaa caaggtttca atgataatta agcaaaattc       60
gatatgccca aacttacaaa gtaagctcaa caagtacaat gctcacatat ctatgcacat      120
gttcaattac aaaacatttg tatactatcc taacacattc tacacaaaca aaaagcgctt      180
ttacatccac tattgccaaa caggatctac gaaaccacta caacccaac gcacattgac       240 taatacgaga acaactaaat gaatagaact ccgaataaaa aaatcatcaa taaaacaatg      300
gcagaaaaaa cgcaaaacat tgtgatctgt ttgttgtttt ggtgaacccg cgcggccatc      360
atcgcacgcg ctccgaccgn ggacagtcgt catcgctcac cgccggcgag cgccacggat     420
accaaacccg ctttccccg aacaaagcgc gccaccttcc cgccaaccgt acgaggacag      480
cggtggcggc gcgaatgccg gagaggcgac tccggcagcc gcggcgccgc cggacggcaa     540
gctcagataa gatcaagtag tgttcgtgag gtcgaaacc ctagctcgcc gcctcctccc     600
ccacggcctt tttacaagcg aaaaacggcg cccaccaaat gggctcgcga aggcccaact    660
gattctagcc cagcccataa tggcccacta actatccccc atgggcccact agagctaaac     720 cctaatcccc tcgctataaa atcgctctct cgaagcgatc tctcccttc gccgccgcct     780 ctctcccgca ccaacctgcc tgagccctag tcgccgccgc cgccgcgcgc caccactgca     840
accatggccg ccgcgctcac ccgcccgcct ccaggcacgg tccagtgctt cgggcgcaag     900
aagacggcgg tggccgtctc ctactgcaag ccggggcgcg ggctgatcaa ggtgaacggc     960
gtcccgatcg agctgatcag gccggagatg ctc                                  993
```

<210> SEQ ID NO 9
<211> LENGTH: 817
<212> TYPE: DNA
<213> ORGANISM: Oryza sativa

<400> SEQUENCE: 9

```
gtctggctac aaatctatag ctctctgctc ttctcctctc ttttattttc ttaaaatatg       60
ttcgtagtta gcttatagtc tactattgta cctggtctta gttagtatct tgtatttaag     120
tgaatgcttt actcgtaata actttattac attaacatac gatgaattta aaatgataaa     180
ggtaatatgc atgagataaa gctcgtcaac aagccagctc gcgagctgag acgctgtttt     240
tagctcggaa tcatggagaa attcagcatg cagcatcaac taaaaacccc actttgctca     300
```

```
aagatttta gccttgttag tcaacaatag ttttcatcac ctaacaaacg ggttgtactg    360
taagtttgta acagagatca caccgaatgg atgggcagca aaaatgcagg gtaaaaccaa   420
agaagggtgg aaggaatgaa ccttctgctc cccccaacag aaaaaatgac agcagaaaac   480
aaaccagtct gcaacctact aagctttgta gtcttccctc atgccgtcgt ccctgcaat    540 cctgaatcca acaacctcc aggagttgca aaatcttccc ctattaaagc acaccacaaa   600
gcatgctgcg attgcactgt cacaccagcg aaatcacagg actagaatac ttgctgacta   660
ctgaggcgaa aggataccgg gtggcgaaga tggctgacct tggattcggc gatgccagga   720
gtggcaatgg cagcaggagc caatgctcca gggggaaggc gatgctgctc gccctcggca   780
agggcctccc tgagcaagtt cttccccagg agtaggt                            817

<210> SEQ ID NO 10
<211> LENGTH: 303
<212> TYPE: DNA
<213> ORGANISM: Oryza sativa

<400> SEQUENCE: 10
caacgaactg cgagtgattc aagaaaaaag aaaacctgag ctttcgatct cttcggagtg    60
gtttcttgtt ctttgaaaaa gaggggggatt aatggcgaca gccgggaagg tgatcaagtg   120
caaagcggcg gtggcatggg aggccgggaa gccgctgtcg atcgaggagg tggaggttgc   180
gccgccgcag gccatggagg tccgcgtcaa gatcctctac accgccctct gccacaccga   240
cgtctacttc tgggaggcca aggggcaaac acctgttttc cctaggatct tgggccatga   300
aga                                                                 303

<210> SEQ ID NO 11
<211> LENGTH: 895
<212> TYPE: DNA
<213> ORGANISM: Oryza sativa
<220> FEATURE:
<221> NAME/KEY: misc_feature
<222> LOCATION: (1)..(895)
<223> OTHER INFORMATION: n = a, c, g, or t.

<400> SEQUENCE: 11
tggtgtcatt ggtgctgata gatgtgatgc ccacacctca gggntccgcg cgccatggtg    60
agcanccggt gaatcttccg ccggctcttg tccttccgtc gtctgaccag ataaggttnt   120
cccctntgat taccccccatt gctacctaag ttggtgattc attggtagat ctacttgtgg   180
tttaatgtgc angaatgctn ggtagatctg gttgttggng aaagtgcaag aatgcannaa   240
tgaatggtgt gaactaatgc atatatcctg gtntgcgtat ttcaaagtac tgtgcatatg   300
tgtattatac acaagttagc atgcacattg atctttgcct cttttgccgt angccctagn   360
atgcatatgt gtnttatacc atnctgtatt atgtacttat attataatgt gaaattatat   420
gtggaatgct ccantgcana tttgctcttg gttaattagt ttaggaaaaa ttgcaaatat   480
gatcttgtga gaatttgtga agtacataga aggcaatttg ttttgacaat gaagtatggt   540
ttgttgtttg ttcatttagt tctccgtaat actgcctaaa tttaaatgta tgtttggtga   600
actgaaataa gatatggtta gtgatgtcat agttttttaa cgactatttg tccttgtgag   660
taaggttgtc attcctcagg tttactgcct ttagtgtggn tatatgtctc ccaaacctga   720
gaaaacgagg aatgtgatag cagccgagaa attgaccatg tttcctcccc cccgcctctt   780
ttgctttcct antaggtttt gcaataattt ttggcatgac aatcttaatt atgtcctata   840
gtctaaaacc cacaaaaaca tcagaaatcc gntaagaata aattaagtaa agaac        895
```

```
<210> SEQ ID NO 12
<211> LENGTH: 1046
<212> TYPE: DNA
<213> ORGANISM: Oryza sativa
<220> FEATURE:
<221> NAME/KEY: misc_feature
<222> LOCATION: (1)..(1046)
<223> OTHER INFORMATION: n = a, c, g, or t.

<400> SEQUENCE: 12
atggagggaa agaggactac cacttcgatg gtgatcatgt gcatggtcat cttgagcctc      60
actgtcgact acgccaccgc agcacagtgc ggctgctgca tatcctctcg agcaaaagca    120
tgttgttttg gttgtattgc tgctggtggc tccgactcag tctgcaagaa cacttgttgt    180
ttcccatgta ttctggccga ttctgttgtt gctaagatgg acgaaaatgg gagttcttgc    240
taagatggac gaaatgggag ttcttgttaa gatggaagga caagcctaaa acaacatgct    300
tgcattgcta ccagtcttaa tgcctatcat aagaatatgt tgttttgctt caagttatgg    360
ccaagttatg ttaatgttat cttcaataaa ttattgncca tatgggacga tctatagtgg    420
atccatctgt tggtctcaac tctatgtatg tcgtgcatgt gtgctctcac aagcatattt    480
aatttctctt gctgctttta ataaggccat agcactgtcc attgtgtcat ccgatggtct    540
ctgaccttag caatttatta cgacatgatt aatattattt gtgtatgcat gttctttact    600
taatttattc ttancggatt tctgatgttt ttgtgggttt tagactatag gacataatta    660
agattgtcat gccaaaaatt attgcaaaac ctantaggaa agcaaaagag gcggggggga    720
ggaaacatgg tcaatttctc ggctgctatc acattcctcg ttttctcagg tttgggagac    780
atatanccac actaaaggca gtaaacctga ggaatgacaa ccttactcac aaggacaaat    840
agtcgttaaa aaactatgac atcactaacc atatcttatt tcagttcacc aaacatacat    900
ttaaatttag gcagtattac ggagaactaa atgaacaaac aacaaaccat acttcattgt    960
caaaacaaat tgccttctat gtacttcaca aattctcaca agatcatatt tgcaattttt    1020
cctaaactaa ttaaccaaga gcaaat                                         1046
```